US 11,141,117 B2

(12) United States Patent
Chmeissani Raad et al.

(10) Patent No.: US 11,141,117 B2
(45) Date of Patent: Oct. 12, 2021

(54) SYSTEMS AND METHODS FOR MONITORING METABOLIC ACTIVITY AND DETECTORS FOR DETECTING PHOTONS

(71) Applicant: INSTITUT DE FISICA D'ALTES ENERGIES, Bellaterra (ES)

(72) Inventors: Mokhtar Chmeissani Raad, Barcelona (ES); Machiel Kolstein, Barcelona (ES)

(73) Assignee: INSTITUT DE FISICA D'ALTES ENERGIES, Bellaterra (ES)

(*) Notice: Subject to any disclaimer, the term of this patent is extended or adjusted under 35 U.S.C. 154(b) by 340 days.

(21) Appl. No.: 16/319,131

(22) PCT Filed: Jul. 27, 2017

(86) PCT No.: PCT/EP2017/069017
§ 371 (c)(1),
(2) Date: Jan. 18, 2019

(87) PCT Pub. No.: WO2018/019941
PCT Pub. Date: Feb. 1, 2018

(65) Prior Publication Data
US 2021/0007682 A1    Jan. 14, 2021

(30) Foreign Application Priority Data
Jul. 28, 2016 (EP) .................... 16382368

(51) Int. Cl.
*A61B 6/03*   (2006.01)
*A61B 6/00*   (2006.01)
*G01T 1/29*   (2006.01)

(52) U.S. Cl.
CPC ............ *A61B 6/037* (2013.01); *A61B 6/4057* (2013.01); *A61B 6/4266* (2013.01); *A61B 6/482* (2013.01); *A61B 6/5205* (2013.01); *G01T 1/2907* (2013.01)

(58) Field of Classification Search
None
See application file for complete search history.

(56) References Cited

U.S. PATENT DOCUMENTS 6,362,482 B1   3/2002   Stettner et al.
6,484,051 B1   11/2002  Daniel
(Continued)

FOREIGN PATENT DOCUMENTS

DE    102005037902 A1    2/2007
FR    2793954 A1         11/2000
(Continued)

OTHER PUBLICATIONS

International Search Report and Written Opinion dated Nov. 28, 2017 for PCT/EP2017/069017, 14 pages.
(Continued)

*Primary Examiner* — Hoon K Song
(74) *Attorney, Agent, or Firm* — Squire Patton Boggs (US) LLP

(57) ABSTRACT

Examples of systems and methods for monitoring metabolic activity and detectors for detecting photons are disclosed. The methods can include detection in a front and a rear detector of a photon to determine a Compton cone. This Compton cone may be combined with further Compton cone, or Line of Response calculation to determine an origin of nuclear decay. In examples of the systems and methods, substantially real-time visualization of nuclear decay can be achieved.

20 Claims, 12 Drawing Sheets

(56) References Cited

U.S. PATENT DOCUMENTS

| | | | |
|---|---|---|---|
| 6,586,744 | B1 | 7/2003 | Griesmer et al. |
| 8,497,484 | B2 | 7/2013 | Chmeissani et al. |
| 2003/0006376 | A1 | 1/2003 | Tumer |
| 2005/0061984 | A1 | 3/2005 | Hoffman |
| 2007/0057191 | A1* | 3/2007 | Ueno ............... G01T 1/2985 |
| | | | 250/370.09 |
| 2008/0042070 | A1 | 2/2008 | Levin |
| 2008/0240339 | A1 | 10/2008 | Du et al. |
| 2009/0290680 | A1 | 11/2009 | Tumer et al. |

FOREIGN PATENT DOCUMENTS

| | | |
|---|---|---|
| WO | WO 2010/034619 A1 | 4/2010 |
| WO | WO 2012/135725 A2 | 10/2012 |

OTHER PUBLICATIONS

Kolstein et al. "Using triple gamma coincidences with a pixelated semiconductor Compton-PET scanner: a simuation study." *Journal of Instrumentation* 11.01 (2015), XP055337804.

Feng et al. "CBF changes during brain activation: fMRI vs. PET." *Neuroimage* 22.1 (2004): 443-446, XP055337218, ISSn: 1053-8119.

Calderon et al. "Design, development, and modeling of a compton camera tomographer based on room temperature solid statepixel detector." (2014), XP055425178.

Calderon et al. "Evaluation of Compton gamma camera prototype based on pixelated CdTe detectors." *Journal of Instrumentations* 9.06 (2014), doi:10.1088/1748-0221/9/06/C06003.

Calderon et al. "Modeling, Simulation and Evaluation of a Compton Camera Based on a Pixelated Solid-State Detector" *IEEE Nuclear Science Symposium Conference Record*; Orlando, Florida, USA, Oct. 2011, pp. 2708-2715.

Chmeissani et al. "Modeling and Simulation of PET scanner Based on Pixelated Solid-State Detector", , IEEE *Nuclear Science Symposium Conference Record*, Valencia, Spain, Oct. 2009, M10-6, pp. 3496-3502.

Gambhir et al. "A Tabulated Summary of the FDG PET Literature", *Journal of Nuclear Medicine*, 2001, vol. 42, No. 5 (supl), pp. 1S-93S.

Morimoto et al. "Development of a 3D Brain PET Scanner Using CdTe Semiconductor Detectors and its First Clinical Application", *IEEE Transactions on Nuclear Science* published by Nuclear & Plasma Sciences Society, Albuquerque, New Mexico, USA, Oct. 2011, pp. 2708-2715, vol. 58, No. 5, pp. 2181-2189.

Olcott et al, "Data acquisition system design for 1 mm3 resoluttion PSAPD-based PET system", *2007 IEEE Nuclear Science Symposium Conference Record*, pp. 3206-3211.

Shehad et al. "Small Animal PET Camera Design Based on 2-mm Straw Detectors", *2006 IEEE Nuclear Symposium Conference Record*, Piscataway, NJ, USA, Oct. 1, 2006, pp. 2462-2468.

Visvikis et al. "Monte Carlo based performance assessment of different animal PET architectures using pixelated CZT detectors", *Nuclear Instruments and Methods in Physics Research A*, Sep. 2006, vol. 569, pp. 225-229.

International Search Report dated Dec. 16, 2009 for PCT/EP2006/061663, 6 pages.

Written Opinion of the International Searching Authority Report dated Dec. 16, 2009 for PCT/EP2009/061663, 10 pages.

International Preliminary Report on Patentability dated Mar. 4, 2011 for PCT/EP2009/061663, 10 pages.

Kapton, entry from Wikipedia, the free internet encyclopedia, accessed and downloaded Mar. 5, 2013, pp. 1-4; http://en.wikipedia.org/wiki/Kapton.

\* cited by examiner

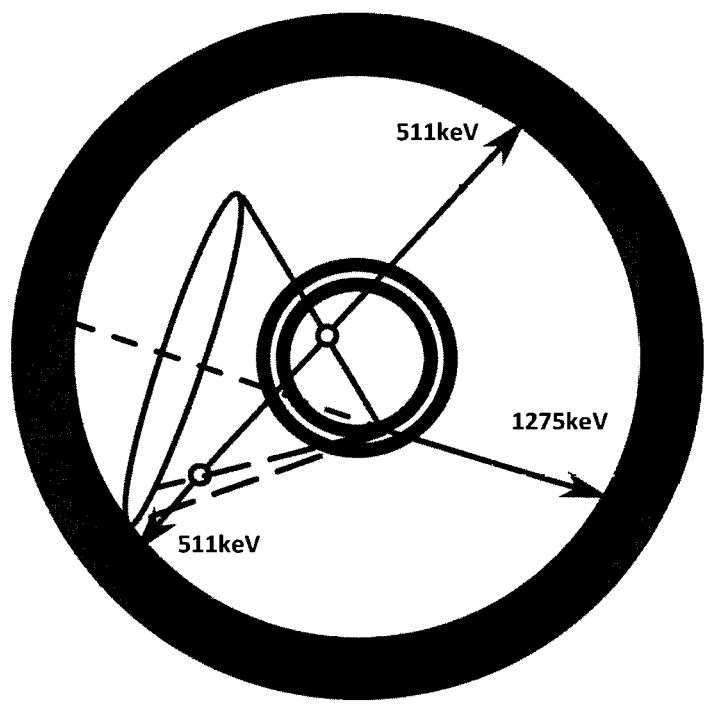
Fig. 2b
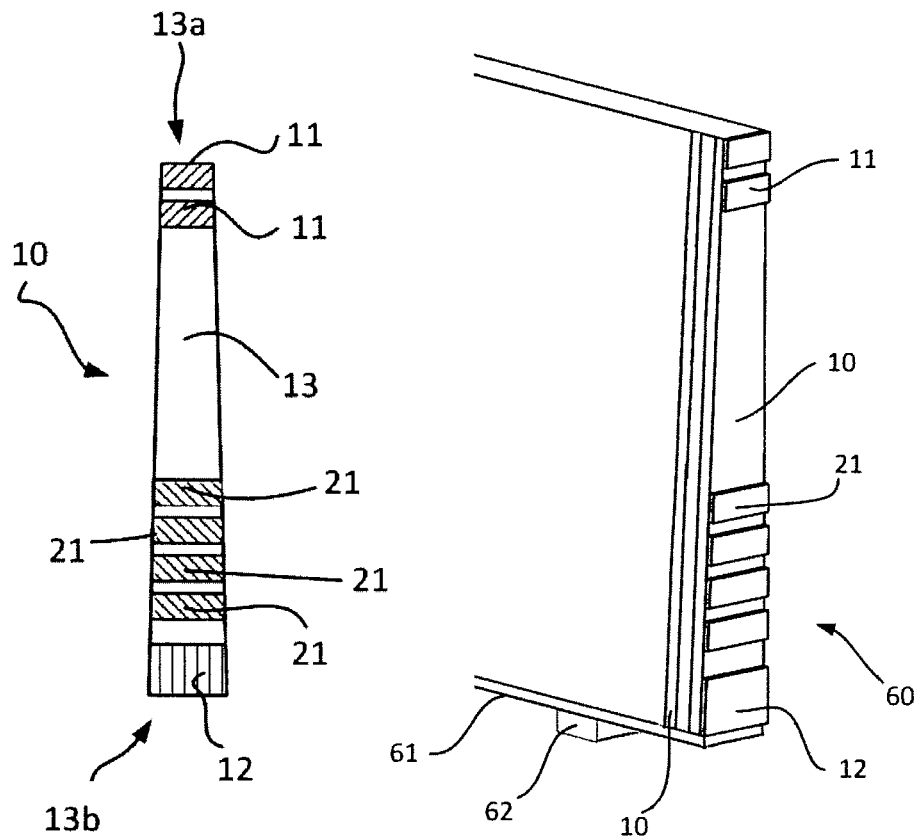
Fig. 3a
Fig. 3b

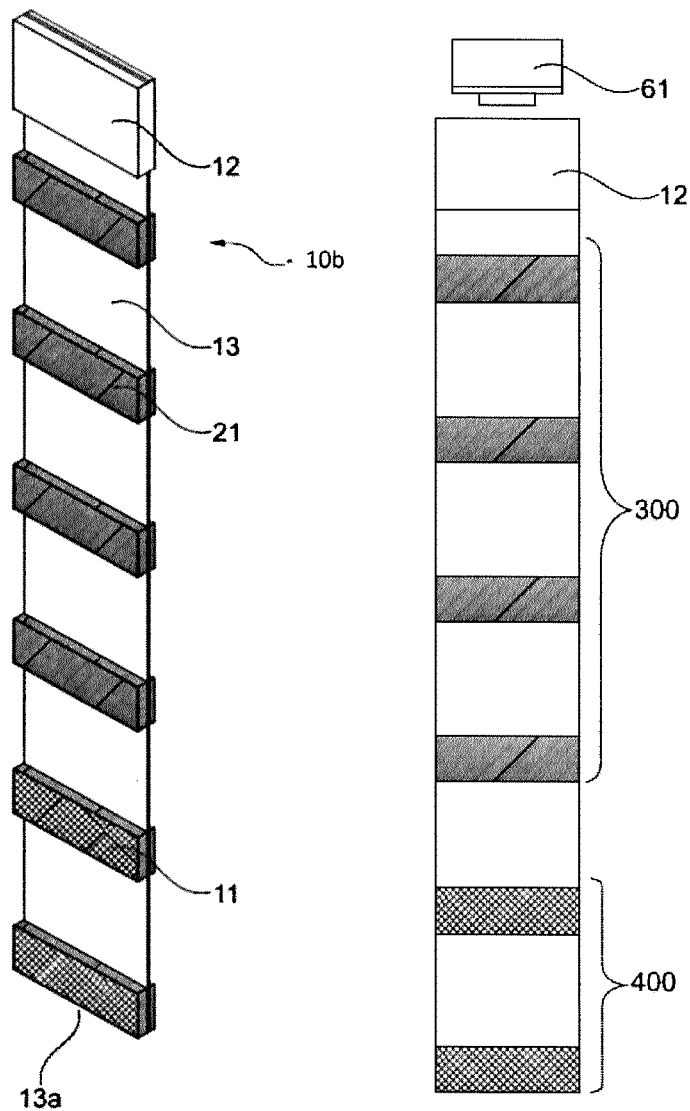
Fig. 6a
Fig. 6c
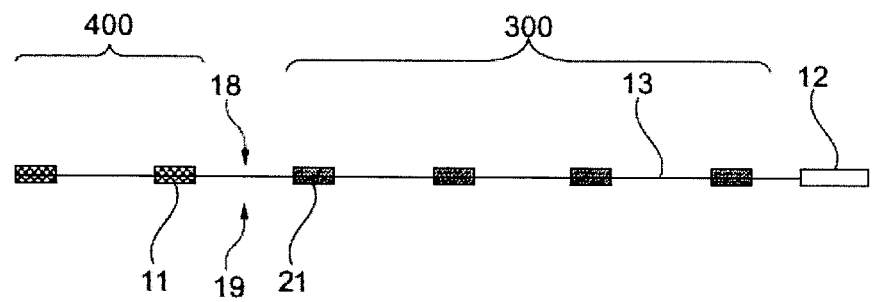
Fig. 6b

SYSTEMS AND METHODS FOR MONITORING METABOLIC ACTIVITY AND DETECTORS FOR DETECTING PHOTONS

The present disclosure claims the benefit of European patent application EP 16 382 368.5 filed on Jul. 28, 2016.

The present disclosure relates to detectors for detecting photons, in particular highly energetic photons. The present disclosure also relates to systems and methods for monitoring metabolic activity. In particular, the present disclosure provides examples of methods and systems for determining and displaying areas showing increased metabolic activity substantially in real-time. The present disclosure further provides examples of detectors suitable for these methods.

Examples of the herein disclosed systems and methods can provide true 4D(x,y,z,t) PET scanning without the use of other imaging modalitity such as MRI, which can be of significant value for better understanding neuroscience.

BACKGROUND

One known method for measuring or determining brain activity uses electroencephalography (EEG) which relies on electrodes placed along the scalp. EEG measures voltage fluctuations resulting from ionic current within the neurons of the brain.

In some cases, it is known to use an invasive approach, in which needle-like probes are inserted inside the brain of an animal to detect signals.

Other known methods include e.g. PET scans and fMRI. Functional magnetic resonance imaging or functional MRI (fMRI) is a functional neuroimaging procedure using MRI technology that measures brain activity by detecting changes associated with blood flow. This technique relies on the fact that cerebral blood flow and neuronal activation are coupled. When an area of the brain is in use, blood flow to that region also increases.

A brain positron emission tomography (PET) scan is an imaging test that allows doctors to see how a patient's brain is functioning. The scan captures images of the activity of the brain after radioactive "tracers" have been absorbed into the bloodstream. These tracers are "attached" to compounds like glucose (sugar). Glucose is the principal fuel of the brain.

Active areas of the brain will be utilizing glucose at a higher rate than inactive areas. The nuclear decay of the radioactive tracer can be pinpointed to specific areas of the brain using a PET scan.

Like other diagnostic techniques in Nuclear Medicine, PET is based in detecting and analyzing the distribution inside the body of radioisotopes which have previously been administered to a patient. The radioisotopes may e.g. be injected into the patient's blood.

Several positron-emitting radioisotopes for medical use are known. The most commonly used is Fluorine-18, which is capable of joining a glucose tracer to get 18-fluoro-deoxy-glucose (18F-FDG). In this way, glucose that is detectable by the emission of radioactive signal is obtained.

After administration of the radioisotopes, the radioisotopes spread throughout the area of the body to be examined and tend to be taken up by e.g. cancer cells. However, the tracers also concentrate in the areas of the brain where the consumption of glucose is relatively high. The systems and methods of the present disclosure are based upon this latter phenomenon.

When the radioisotope decays, it emits a positron which after a few millimeters, or after even less than 1 mm annihilates with an electron. This produces a pair of gamma ray photons moving in opposite directions, each photon having an energy of 511 keV. This pair of gamma ray photons can be detected using a so-called PET scanner. Using the location of detection of both gamma ray photons, the Line of Response (LOR) (which is the line connecting the two locations of detection of the gamma photons) can be reconstructed. This procedure is schematically illustrated in FIG. 1.

FIG. 1 shows a conventional PET scanner 1, in which a bed 3 is provided. Upon this bed, a body 2 of a human or an animal is schematically indicated. Along the perimeter of the PET scanner, a plurality of detectors 4 is provided. The gamma ray photons which move in opposite direction are detected respectively by detector 4a and detector 4b. Using this detection, the LOR can be reconstructed. For a scan of a body part, e.g. the brain, such a body part, e.g. a subject's head may be stabilized and immobilized in a predetermined position to make sure the subject stays still. However, from a single event the precise origin (location of radioactive decay) cannot be determined: the origin might be located anywhere along the LOR.

After collecting millions or 100 millions of such events and using dedicated image processing software for PET, a 3D image is obtained showing concentration of the radio-isotope and therefore an area of brain activity. The PET scanner is usually coupled to a computer, which is responsible for measuring the amount of radioisotopes absorbed by the body, and determining the LOR's. The origin of the events, i.e. the location where the radioactive decay occurs and thus the location where the brain is assumed to be more active, may then be displayed in an image, e.g. on a screen or print-out. It would be beneficial in many different types of PET imaging if the imaging could take place substantially in real-time and with good spatial resolution and energy resolution in order to observe metabolic processes in real-time.

Each radioisotope has a characteristic decay in terms of half-life and in terms of its radiation, e.g. positron, gamma rays with specific energy level or even positron and gamma rays. When e.g. a specific type of cancer is suspected, a doctor might administer a radioisotope that is known to attach particularly well to that kind of cancer cells. To gain a better understanding of the type of cancer, various isotopes might be administered at the same time.

Depending on which body part is to be examined, and in some occasions depending on the size of a patient, a PET scanner and/or a Compton camera may be used. A Compton camera has two detection planes. Photons emitted from the source are scattered in the first plane (Compton scattering) and absorbed in the second plane (photoelectric effect). In both planes the position of the interaction and the energy deposited are measured. The detectors are operated in coincidence, so that only photons that interact with both detectors and deposit a total energy within a given time window are recorded. Using the location of detection and the energy of the photon, the point of origin of the photon can be calculated, using the so-called Compton formula.

In nuclear medical imaging (of the brain or of other body parts or organs) it is beneficial that all or most or many of the events are detected. If more of the events are detected, a smaller amount of isotopes has to be administered. The patient thus will suffer less from possible side effects from the radiation. It is of course important if the precise position of decay can be detected, i.e. high spatial resolution. Or, if the same normal dose is used, the image can be acquired in less time and hence reduce possible image smearing related to patient movements.

An advantage of using EEG for monitoring brain activity is that it can show brain activity in real-time. On the contrary, PET and fMRI have a time resolution between seconds and minutes. Particularly, in PET scans, because many events occur at the same time and one needs to link two separate impacts of gamma rays to the same event, image reconstruction algorithms are needed to reconstruct an image of the activities in the body under study.

Other advantages of EEG include the fact that the subject is not exposed to either radioisotopes or a strong magnetic field. Moreover, EEG as compared to fMRI is silent, which is useful for e.g. measuring response to auditory stimulation. On the other hand, the spatial resolution with EEG is significantly lower than the obtainable spatial resolution with the other methods.

fMRI has an important disadvantage in that it is noisy and can be experienced as claustrophobic.

It is an object of the present disclosure to provide examples of systems and methods for monitoring brain activity based on PET technology that avoid or significantly reduce one of the major disadvantages of PET mentioned before, namely the poor time resolution. It is a further object of the present disclosure to provide examples of systems and methods for monitoring metabolic activity based on PET technology substantially in real-time.

Substantially in real-time herein means that metabolic activity can be monitored (and displayed) to a researcher as decay takes place. The positions of individual events of decay as an indication of a change in metabolic activity can be visualized.

For example, for monitoring brain activity, this means that brain activity can be displayed on the same time scale as stimuli used in such research. A researcher will thus be able to link a possible change in brain activity to a specific stimulus.

U.S. Pat. No. 6,484,051 discloses a Compton imager and methods for generating three-dimensional images. The Compton imager detects Compton scattering of simultaneously or nearly simultaneously emitted gamma rays produced by a radio-nuclide. A possible location of each radio-nuclide decay is defined by the intersection of Compton direction cones corresponding to the detected gamma rays. Three-dimensional images are generated by superposition of individual locations of separate radioactive decay locations.

It is a further object of the present disclosure to provide examples of detectors for detecting photons that have both high spatial and high energy resolution.

It is a further object of the present disclosure to provide examples of improved Compton cameras, Compton imaging, and Compton-PET imaging.

It is a further object of the present disclosure to provide examples of methods and systems that allow the reduction of the dose of radioisotopes administered to a patient.

SUMMARY

In a first aspect, a detector for detecting photons is provided. The detector comprises a plurality of detector modules forming a front detector and a rear detector. The detector modules comprise a plurality of detector devices, and an Interface, the detector devices having a substrate extending from a front end to a rear end, and carrying a plurality of pixelated semiconductor detector slabs, and being arranged such that the front end is closer to a source of the photons than the rear end. The semiconductor detector slabs are arranged on readout circuits, and the detector devices have an input/output element at or near the rear end of the substrate. A front group of one or more of the semiconductor detector slabs arranged close to the front end of the substrate are made from a semiconductor material configured to promote photon scattering and form the front detector, and a rear group of one or more of the semiconductor detector slabs arranged closer to the second end of the substrate than the front group are made from a semiconductor material configured to promote photon absorption, and form the rear detector.

The arrangement of the front and rear detectors makes the detector suitable for Compton imaging. With the detector according to the first aspect, the front and rear detector slabs are arranged on common substrates with the readout circuit arranged directly underneath the semiconductor slabs. The readout circuit can be attached to the semiconductor via bonding or gluing or otherwise. The input/output element is provided at or near the rear end of the substrate, so that no parasitic elements or electronics are arranged between the front and the rear detector.

In some examples, the substrate may be a kapton layer, in particular a thinned kapton printed circuit board.

In some examples, a distance between the rearward most detector slab of the front detector and the forward most detector slab of the rear detector may be greater than a distance between the detector slabs of the front detector and than a distance between the detector slabs of the rear detector. An increased distance between the front and rear detector can increase the accuracy of the Compton cone calculation and lead to better spatial resolution.

In some examples, the distance between the rearward most detector slab of the front detector and the forward most detector slab of the rear detector is between 10 and 30 centimetres, specifically between 10 and 20 centimetres.

In some examples, the detector slabs of the front detector may be made from silicon. Generally speaking, low Z semiconductor material is suitable for promoting photon scattering, whereas high Z semiconductor material is suitable for promoting photon absorption. High Z semiconductor material is therefore more suitable for the outer detector. In some examples, the detector slabs of the outer detector may be made from CdTe or CdZnTe. Other suitable semiconductors can include GaAs, TlBr, PbS, $CaTiO_3$ or $HgI_2$.

The atomic number or proton number (symbol Z) of a chemical element is the number of protons found in the nucleus of an atom. It is identical to the charge number of the nucleus. Low Z semiconductor material may be regarded all throughout the present disclosure as a semiconductor having Z below 20. High Z semiconductor material may herein be regarded as a semiconductor having Z above 20.

In some examples, the front detector and rear detector have a substantially circular cross-section, and the substrates of the detector devices have an Isosceles trapezoidal shape. In this aspect, a particularly beneficial PET detector can be provided. The front detector and rear detector may thus be arranged as concentric annular detectors, the front detector being the inner detector ring and the rear detector being the outer detector ring.

In a further aspect, a method for real-time visualization of metabolic activity in a subject using annular inner and outer ring detectors (i.e. a PET detector arrangement) is provided. The subject has previously been administered a radioactive tracer and positioned such that a portion of a body of the subject is at least partially provided within a photon detector field of view (FOV). The method comprises detecting radioactive decay of the tracer within the photon detector, calculating a position of an origin of the radioactive decay and displaying the position of the origin of the radioactive decay substantially in real-time. The radioactive tracer comprises a radioactive isotope which in decay emits a positron and a separate gamma ray, and the photon detector comprises an inner ring detector, and an outer ring detector. Impacts of photons in the inner and outer ring detectors belonging to the same event of radioactive decay, wherein the separate gamma ray is detected in both the inner and the outer ring detector can be detected. And in relation with the impacts belonging to the same event of radioactive decay Line-of-Response calculation and Compton cone calculation based on Compton scattering from the inner ring detector is used to calculate an origin of the event.

In this aspect, real-time visualization of metabolic activity is made possible by making use of specific radioactive isotopes (e.g. $^{22}$Na, $^{44}$Sc, $^{48}$V) that in decay emit a positron and an additional gamma ray. The positron quickly annihilates with an electron to produce two back-to-back gamma rays moving in opposite directions. The Line of Response of these back-to-back gamma rays may be calculated in a "classical" way. In the present method, the additional information that the additional gamma ray can provide is used to more quickly determine the origin of radioactive decay (i.e. the location of the isotope, which can indicate an area of increased metabolic activity). In a classical way for any two back-to-back gamma rays, there are an infinite number of positions along the Line of Response from which the impacts may originate. It is only by combining thousands of Lines of Response that the origin of decay can be determined. In the method herein provided, the additional gamma ray can provide for a single event the information to determine the point along the Line of Response that is the origin of the decay.

In accordance with this aspect, also events based on random coincidences (i.e. two separate gamma rays are detected at the same time but actually do not belong to the same event: the LOR calculation in this case would render a wrong result) can be excluded. The angle measured in Compton scattering cannot be reconciled with the apparent LOR. The extra Information from Compton scattering can thus be used to discard such random events.

In some examples, specific events complying with specific rules of energy deposits may be selected and linked together. For example, events in which two back-to-back gamma rays are detected in the outer ring or rear detector, and a separate gamma ray scatters in the inner or front detector and is detected both In the inner/front and in the outer/rear detector may be selected and separated from other events. The calculation of these specific events comprises LOR calculation for the back-to-back gamma rays, and Compton cone calculation for the separate gamma ray. The intersection of the Compton Cone with the LOR determines the point of origin.

In some examples, calculating the position of the origin of the radioactive decay may furthermore comprise determining energy deposits of the at least four impacts. The energy deposits may be used to determine impacts that belong to the same event. For example, the energy of the separate gamma ray is known for specific isotopes, e.g. 1274.5 keV for $^{22}$Na. If the separate gamma ray scatters in the Inner detector and is detected in both the inner and outer detector, the photons of these impacts must have a total energy corresponding to approximately 1274.5 keV. Separate impacts can thus be linked to the same event, based also on a timestamp of the registered Impacts. Similarly, back-to-back gamma rays only detected in the outer detector each must have an energy deposit of approximately 511 keV to qualify as the same event. Similarly again, if one of the back-to-back gamma rays is scattered and detected by both the inner and the outer detectors, the energy deposits must have a sum of approximately 511 keV in order to be recognized as originating from the same event.

However, the use of this radioisotope Is merely one example of the use of a detector as herein described. In yet a further aspect, a method for real-time visualization of metabolic activity in a subject using front/inner and rear/outer detectors is provided. The subject has previously been administered a radioactive tracer which in decay emits three separate gamma rays and the subject is positioned such that a portion of a body of the subject is at least partially provided within a photon detector field of view (FOV). The method comprises detecting radioactive decay of the tracer within the photon detector, calculating a position of an origin of the radioactive decay and displaying the position of the origin of the radioactive decay event by event in quasi real-time. The photon detector comprises an inner ring/front detector, and an outer ring/rear detector. Scattering and absorption of photons in the inner/front and outer/rear detectors respectively belonging to the same event of radioactive decay can be detected. And in relation with the impacts that belong to the same event of radioactive decay Compton cone calculation for the three gamma rays based on Compton scattering from the inner ring/front detector and absorption in the outer ring/rear detector is used to calculate an origin of the event.

In this aspect, real-time visualization of metabolic activity is made possible by making use of specific radioactive isotopes e.g. $^{94}$Tc that in decay emits three gamma rays. $^{94}$Tc in decay emits three gamma rays at 701 keV, 849 keV and 871 keV. $^{94}$Tc is however merely one example of a radioisotope that may be used in this aspect.

The three separate gamma rays, in some cases, may scatter in the front/inner detector and be absorbed in the rear/outer detector. The events in the front/inner detector and rear/outer detector linked to the same gamma ray may be linked together based on the energy deposits in the separate detectors. The origin of the decay can immediately be determined by Compton cone calculation for each of the three gamma rays. The three Compton cones will intersect at a single point, which is the origin of the nuclear decay. Again, as compared to "classic" PET scanners or "classic" Compton cameras, the need to combine many events together to determine the origin of decay is obviated with the detector as herein provided.

It should be clear however, that the detectors as herein provided may be used in combination with many different radioisotopes with different decay characteristics.

In a further aspect, a method for real-time monitoring of activity in a brain of a subject is provided. The subject has previously been administered a radioactive tracer, and the method comprises positioning the subject such that the brain of the subject is at least partially provided within a photon detector, providing a stimulus to the subject and a method for real-time visualization according to examples of the previous aspect.

In this aspect, a researcher may provide different kinds of stimuli to a subject. Thanks to the fact that the position of radioactive decay can be calculated and visualized substantially in real-time, event-by-event, a researcher may see or monitor different areas of the brain that become active in response to the stimuli substantially in real-time. For this type of Imaging even relatively low activity can be used. In response to what is displayed to the researcher, he/she can adapt the stimuli (which might be e.g. tactile, visual, auditory or combinations thereof) in real-time to further the investigation. The spatial resolution of PET scanners may be combined with a temporal resolution to e.g. EEG.

In a further aspect, a system for real-time visualization of metabolic activity in a subject which has previously been administered a radioactive tracer is provided. The system comprises a detector according to any of the examples herein disclosed, and a computing system for determining impacts of photons in the front/inner and rear/outer detectors, for calculating a position of an origin of the radioactive decay. In relation with the impacts Line-of-Response calculation and/or Compton cone calculation based on Compton scattering from the front/inner detector, and for generating a video signal reflecting the origin of the radioactive decay, and a device capable of receiving the video signal and reproducing the video signal on a screen.

In yet a further aspect, a system for real-time visualization of metabolic activity in a subject is provided. The subject has previously been administered a radioactive tracer. The system comprises a photon detector comprising an inner ring detector, and an outer ring detector, and a computing system for determining at least four impacts of photons in the inner and outer ring detectors, for calculating a position of an origin of the radioactive decay using in relation with the at least four impacts Line-of-Response calculation and Compton cone calculation based on Compton scattering from the first detector, and for generating a video signal reflecting the origin of the radioactive decay. Alternatively, in the case of decay with three separate gamma rays as previously described, Compton calculation may be done for three separate gamma rays. The system further comprises a device capable of receiving the video signal and reproducing the video signal on a screen.

In some examples, the screen may show a 3D scatter plot in the volume of interest of a subject (this volume of interest could be the brain as an example) where every dot represents an event of decay. Each dot may last a fraction of a second to make it possible for the human eye to register such a signal. One can also use computer algorithms to sense a small signal and visualize it, which cannot be detected by the naked eye. Such algorithms may be based on changes of statistical significance, e.g. more than 5 standard deviations above nominal conditions or as differential change, over an area of interest In some examples, the screen may show the events of decay (for example in the scatter plot) in combination with a representation of the part of the body of the subject. Such a representation may have been obtained previously in a CT or MRI scan.

In some examples, a digital signal processor connected with the inner and the outer ring detectors may be used for calculating the origin of the radioactive decay, i.e. an area of increased brain activity. Digital signal processors (DSP) may be configured for a specific task and perform this task very rapidly. The calculation of the Line-of-Response, and/or the Compton cones and intersections between them are covered by relatively simple mathematical equations. DSP's may thus provide the speed of calculation needed to be able to monitor brain activity in real-time.

In some examples, a distance between an Inner rim of the outer ring detector (or innermost detecting portion of the outer ring detector) and an outer rim of the inner ring detector (or outermost detecting portion of the inner ring detector) is at least 5 cm, and preferably 10 cm or more. Increasing the distance between the inner and the outer detector reduces the error on the angle that defines the Compton cone, due to the voxel size. This improves the imaging resolution, since this will at the same time reduce the uncertainty or error in the Intersection of the LOR and the Compton Cone

BRIEF DESCRIPTION OF THE DRAWINGS

Non-limiting examples of the present disclosure will be described In the following, with reference to the appended drawings, in which:

FIG. 2b schematically illustrates a calculation of an origin of nuclear decay combining LOR calculation and Compton cone calculation;

FIG. 4b schematically illustrates a process which may be used in a digital signal processor in examples of the system of FIG. 4a;

FIGS. 6a-6c schematically illustrate a further example of a detector device which may be used to build up detectors and may be used in methods disclosed herein.

DETAILED DESCRIPTION OF EXAMPLES

Figure 1:
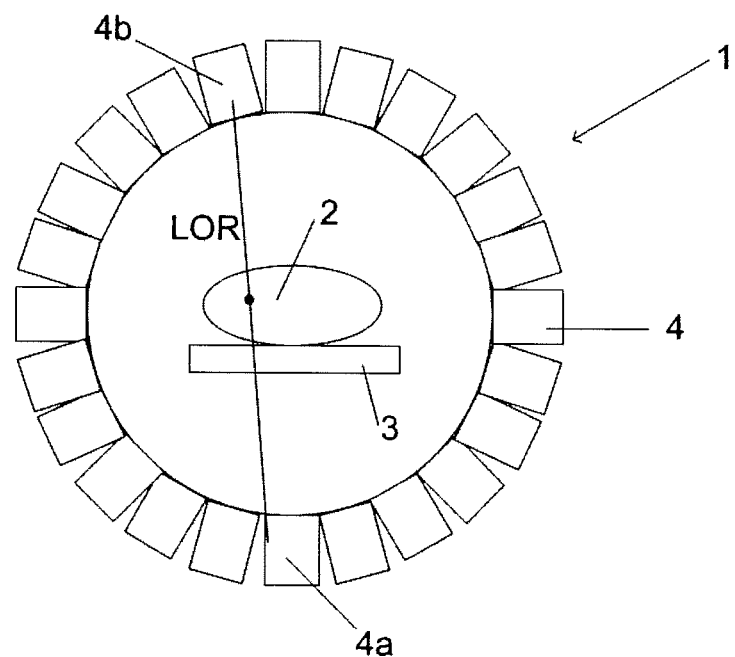
FIG. 1 schematically illustrates the calculation of Line of Response of back-to-back gamma rays as used in PET scanners.

FIG. 1 has been previously discussed.

Figure 2A:
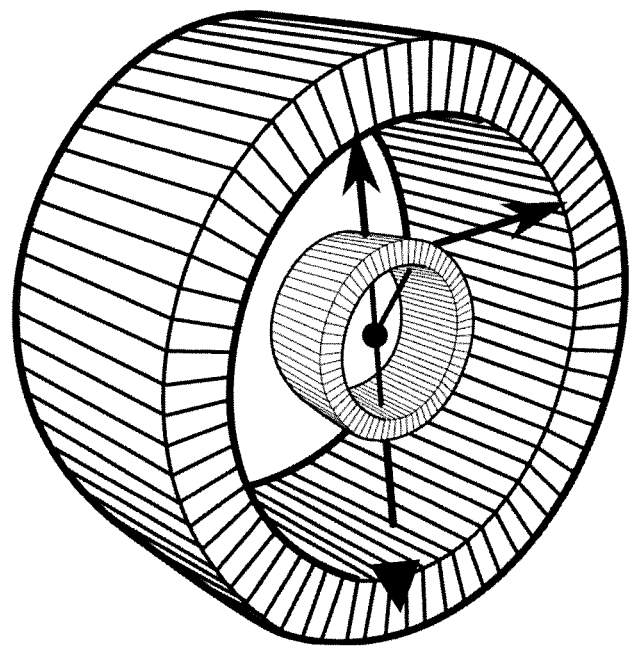
FIG. 2a schematically illustrates a photon detector that may be used in examples of the method and systems for real-time visualization of metabolic activity.

FIG. 2a schematically illustrates a photon detector that may be used in examples of the method and systems for real-time visualization of brain activity. In FIG. 2a, the photon detector includes an inner ring detector and an outer ring detector, circumferentially arranged outside the inner ring detector.

The spatial resolution is related to the pixel/voxel size of semiconductor detector. Examples of such detectors are described e.g. In PCT/EP2009/061633, published as WO 2010/034619. The herein provided detectors are based on the use of detector devices and modules that have certain aspects in common with the detector devices and modules disclosed in this document.

Displayed in FIG. 2a is an event in which the back-to-back gamma rays resulting from positron-electron annihilation are detected in the outer detector. The corresponding additional gamma ray is scattered in the inner detector and is detected in both the inner and the outer detector. The inner detector effectively works as a Compton Camera scatterer. Specific radioisotopes show this behaviour at decay.

FIG. 2b schematically illustrates a calculation of an origin of nuclear decay combining LOR calculation and Compton cone calculation. For the specific type of event displayed in FIG. 2a, a Line of Response may be calculated for the back-to-back gamma rays. A Compton cone may be calculated for the photons detected from the Compton scattering. It may be seen in FIG. 2b, that the Compton cone can intersect in more than one point with the Line of Response. However, only one of these points can actually be the origin of the radioactive decay, namely the point inside the inner ring detector.

FIG. 3a schematically illustrates an example of a detector device which may be advantageously used to build a photon detector, e.g combining the inner and/or the outer ring detector as illustrated in FIGS. 2a and 2b. FIGS. 3g-3i illustrate more details of the build-up of the detector devices, whereas FIGS. 3j and 3k illustrate the build-up of the detector modules and detector systems respectively.

The device 10 for detecting highly energetic photons may comprise a plurality modular pixelated room temperature semiconductor detector slabs 11, 21 in a tiled/stacked scheme. The device 10 comprises a isosceles trapezoidal substrate 13 carrying the semiconductor detector slabs. The substrate has a first front end 13a, and a second rear end 13b. The detector device configured to be positioned with respect to a subject in such a way that the front end 13a is closer to the subject.

In the device of this example, six pixelated detector slabs are shown. Four detector slabs 21 that are closer to the rear end 13b (i.e. and thus further away from the subject) are grouped together to ultimately form the rear detector (and in the case of FIG. 2, the outer detector ring). Two detector slabs 11 closer to the front end 13a are grouped together to ultimately form a front detector (and in the case of FIG. 2, the inner detector ring).

In the example of FIG. 3a, a distance between the rearward most detector slab of the front detector (the second detector slab when seen from the front end 13a towards the rear end 13b) and the forward most detector slab of the rear detector (the third detector slab when seen from the front end 13a towards the rear end 13b) is greater than a distance between the detector slabs of the front detector and also than a distance between the detector slabs of the rear detector.

The distance between the rearward most detector slab of the front detector and the forward most detector slab of the rear detector may be between approximately 10 and 30 centimetres, specifically between 10 and 20 centimetres. The calculation of the Compton cone as previously illustrated with reference to FIG. 2b can be Improved with increased distance between the Inner detector and the outer detector (i.e. the front detector and the rear detector).

A distance between consecutive detector slabs of the front/inner detector may be between 0.5 and 2 centimetres. In the example of FIG. 3, a length of the semiconductor slabs 11 in the direction from the front end to the rear end may be 1 cm. And a distance between the consecutive detector slabs may be approximately 0.5 cm. A distance between the front/inner detector and the rear/outer detector in the example of FIG. 3a may be 10-15 cm approximately.

The front detector slabs 11 are made from a semiconductor material that is configured to promote scattering of photons. A low Z semiconductor material (i.e. Z value below 20) promotes scattering, rather than absorption. The outer detector slabs 21 is made from a semiconductor material configured to promote absorbing photons. A high Z (Z above 20) semiconductor material is configured to promote absorption.

Room temperature semiconductor detectors may be e.g. Si, GaAs, CdTe, CdZnTe, TlBr, PbS, $CaTiO_3$ or $HgI_2$. The inner detector slabs 11 may be made in particular from Silicon. The outer detector slabs in the example of FIG. 3a may be made e.g. from CdTe, or CdZnTe.

Pixelated detector slabs may be used. The approximate size can be of 2 cm×1 cm×0.2 cm for the outermost/most rearward detector slab 21; the pixel size may be approximately of 1 mm×1 mm. Since the shape of the devices 10 is trapezoidal, the dimensions of the detector slabs can vary within the same device. The size of the detectors may also be chosen differently. Using the device with a thickness of 0.2 cm, it is possible to build a thick solid-state detector by combining a plurality of these devices. This detector will however not suffer from problems such as time collection in thick conventional semiconductor detectors.

The trapezoidal shape of the detector device means that the width of the substrate at the first end is smaller than the width of the substrate at the second end.

Six ASICs (application-specific Integrated circuit), one for each semiconductor detector slab 11, 21 can act as readout elements for them. In other examples, it is possible to use more than one ASIC to act as readout element for a single slab. The ASICs and (pixelated) semiconductor slabs may be attached with bump bonding or conductive glue, so that each pixel pad can be connected independently to its own front-end readout channel.

An input/output element connector 12, at the backend of element 10, is connected to the ASICs for data input and output (that is, mainly for obtaining the values generated by the ASICs from the semiconductor detector captured parameters) and a kapton layer 13 which may be a kapton PCB acts as a base layer, upon which the semiconductor detector slabs 11,21, the ASICs, and the input/output element 12 are mounted.

With reference to FIGS. 3g-3i, wire bonding pads 20 may be provided for connecting each individual ASIC 30 to the kapton layer 13, and then to input/output element 12. More specifically, the top plane of the kapton layer 13 is in this example used for mounting the ASICs 30, wire bonding 20, the semiconductor detector slabs 11, and the input/output element 12. In the bottom plane, the kapton layer 13 may comprise connections to a power supply that can provide High voltage to polarize semiconductor detector slabs 11 of a neighbouring second device arranged next to the shown device. The slabs may be piled on the top of each other and the back side of one element 10 that provides the High Voltage and may be connected to the top of the slab in the slab beneath element 10 via double adhesive conducting thin tape.

FIGS. 3b and 3j schematically illustrate a module 60 comprising a plurality of detector devices 10 for detecting highly energetic photons (as illustrated in FIG. 3a) which are connected through their Input/output elements 12 to an interface, which in this case may be a printed circuit board 61 (PCB) The devices are arranged in a row with their large faces adjacent to each other.

The PCB 61 may comprises connectors (e.g. plugs) 62, for example, with low profile, for accessing the ASICs 30, that is, the connectors of the PCB are connected with the input/output signal connectors 12, which have access (through the kapton and wire bonding) to the ASICs. This way, the processed data in the ASICs 30 can be obtained in the connectors and read from them.

Each pixelated semiconductor detector slab essentially can give two dimensional information about where impact with a gamma ray occurred, because they are pixelated in the module, a plurality of devices is arranged in such a way that a three-dimensional semiconductor detector is obtained. Every device is a two-dimensional detector, but by providing a number of devices on top of each other, a three-dimensional detector is obtained.

The working principle of the module 60 is as follows: A gamma ray impacts a pixelated detector. At the point of impact of the captured photon, electron-holes (e-h) are created. Due to the applied high voltage, the e-h drift inducing a signal on the pixel electrode, which is later amplified and processed by the ASIC. The ASIC will indicate the position of the impact point and hence the coordinate of the pixel where Impact occurred. Additionally, the ASIC can provide the energy and the time stamp for the event relative to a global time clock. The interface data bus or PCB 61 has data on which ASIC the event was registered. The PCB thus has data about the coordinate of the voxel where impact occurred.

An impact in this sense can be a scattering, or absorption. Whether or not there is scattering or absorption can be determined from the energy deposited. Scatter events can be linked to each other by checking whether the sum of energy deposits, within the coincidence time window adds up to an amount of energy expected from radiation emitted.

In some examples, spaces between different detector devices may be filled up with lightweight material which is transparent to radiation. In particular, the spaces that may be present between the most rearward semiconductor slab of the front detector and the most forward semiconductor slab of the rear detector may be filled up with such material.

In one example, a cardboard honeycomb material may be inserted in between detector devices to increase the stiffness of the modules. In a further example, aerogel may be used instead.

From a plurality of modules, a detector system 80 can be made as illustrated in FIGS. 3*j* and 3*k*. A detector system 80 comprises a plurality of modules 60. The interface 61 of each of the modules is connected with connectors to interface bus 70. The interface bus 70 may have suitable receptors/sockets for the connectors/plugs of the modules.

Figure 3C:
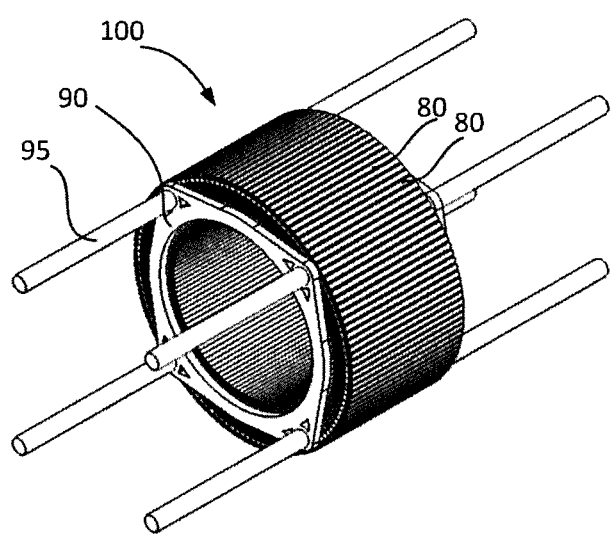
FIGS. 3a-3d schematically illustrate details of devices and modules that built-up a detector and an example of a detector having an inner and outer ring detector.

FIG. 3*c* shows a partial view of a detector 100 including both an inner ring detector and an outer ring detector. The detector 100 comprises a plurality of systems 80 for detecting highly energetic photons. Each of these systems comprises a plurality of the modules 60 schematically illustrated in FIG. 3*b* arranged axially one behind the other. At least some devices of the systems comprise base layers having a shape of an isosceles trapezoid, which allows obtaining the shape of a ring.

Basically, the detector systems 80 are piled to form the ring, that is, the plurality of systems are arranged forming the outer ring detector and inner ring detector with the side edges of the devices 10 adjacent to each other. This way, the shape of the systems forms a hermetic geometry. The detector systems 80 are held together by a support structure comprising front and rear plates 90 clamping the devices/modules together in an axial direction. The plates are held by support bars 95. The support bars may be suspended in a suitable support structure As a result a detector is formed wherein the space between the inner detector ring and the outer detector ring is essentially formed by the layers of kapton (or an alternative suitable substrate for the semiconductor detector slabs 11, 21). In this example, there is minimum of passive material, between the inner and the outer detector, in order not to alter the energy and the direction of the scattered photon.

Figure 3D:
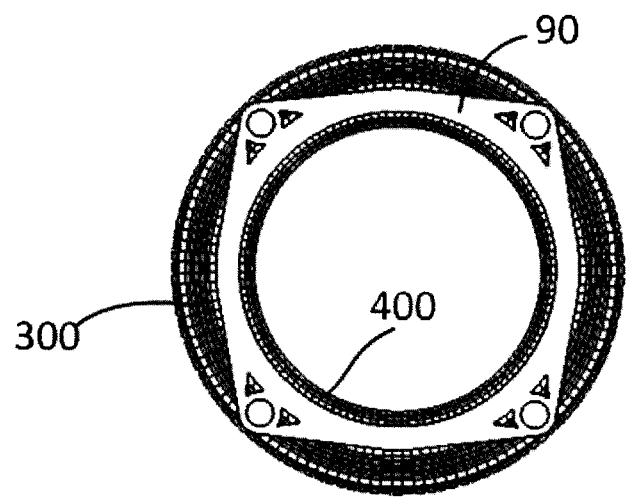

FIG. 3*d* schematically illustrates a frontal view of the same detector.

Figure 3E:
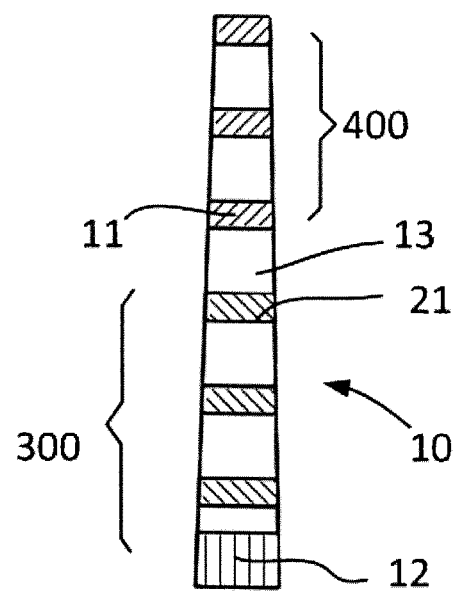
FIG. 3e schematically illustrates an alternative detector device which may be used in examples of detector systems disclosed herein and FIG. 3f schematically results in a PET detector built up from such detector devices.

FIG. 3*e* shows a further example of a detector device 10*a*, that may be used to build modules, and systems, and ultimately a detector as illustrated in FIGS. 3*b*-3*d*. Contrary to what was shown in FIG. 3*a*, in this case, the detectors 11, 21 are evenly spaced on the substrate. In FIG. 3*a*, groups of detectors ultimately forming the inner detector and groups of detectors ultimately forming the outer detector are spaced more closely together.

In the example of FIG. 3*e*, the three inner detector slabs 11 ultimately will form the Inner ring detector 400 and are made from a low Z semiconductor material promoting scattering. The three outer detector slabs 21 will ultimately form the outer ring detector 300 and are made from a high Z semiconductor material promoting absorption. It will be clear that different number of detector slabs may be chosen, and they may be grouped together differently as well.

Figure 3F:
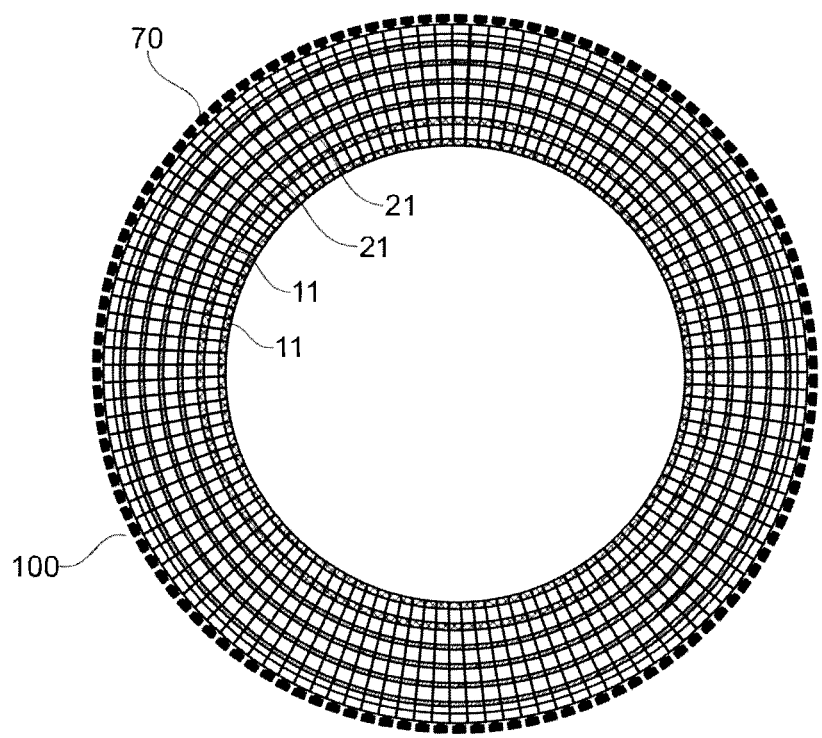
FIGS. 3g-3k schematically illustrate a build-up of devices into modules, and of modules into detection systems and into detectors according to examples of the present disclosure.
Figure 3G:
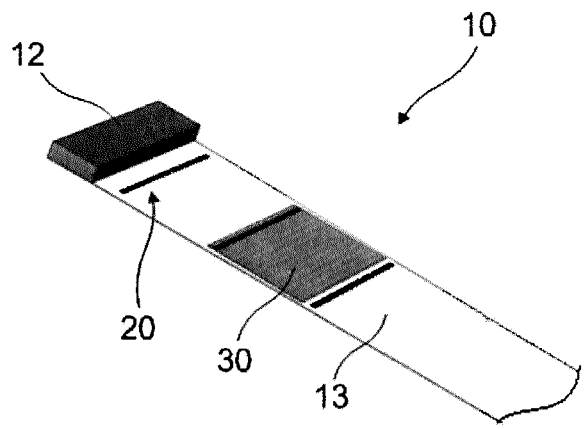
Figure 3H:
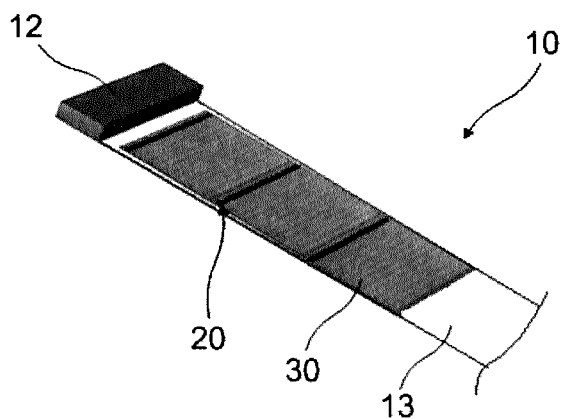
Figure 3I:
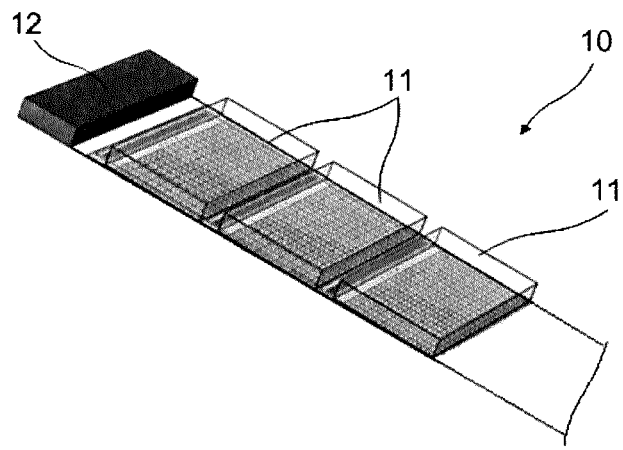
Figure 3J:
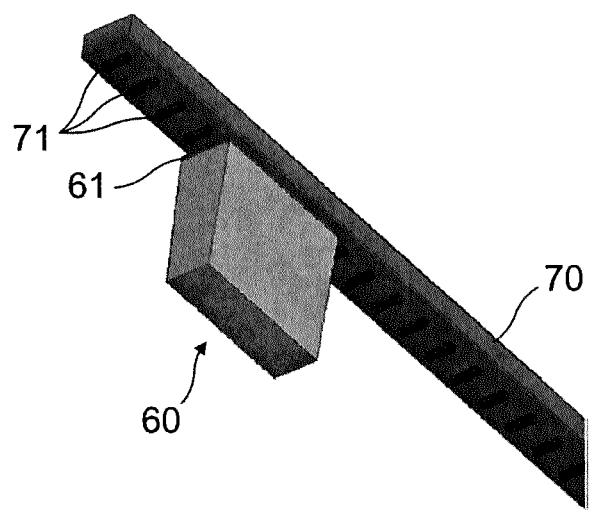
Figure 3K:
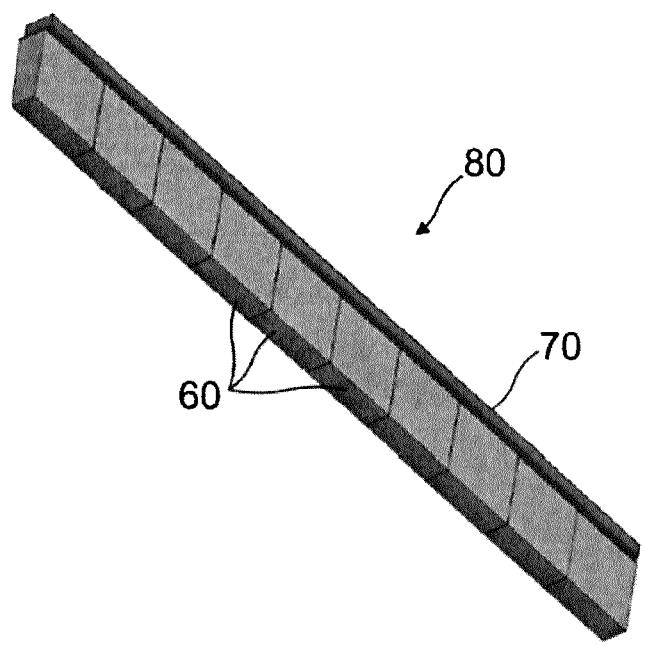

FIG. 3*f* illustrates a further view of the PET detector 100 built up from the detector device illustrated in FIG. 3*e*. FIG. 3*f* shows how semiconductor slabs 11 together form the Inner detector, whereas the outer semiconductor slabs 21 together form the outer detector. Several of the detector devices may be grouped together to form a module. An interface 70 collects data from several modules.

Figure 4A:
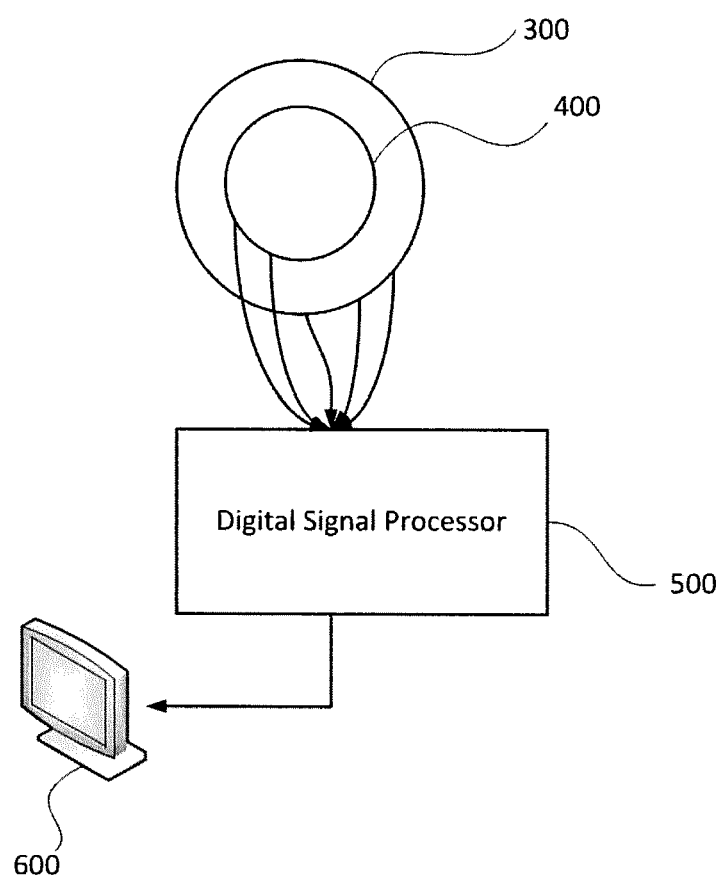
FIG. 4a schematically illustrates an example of a system for real-time visualization of metabolic activity.

FIG. 4*a* schematically illustrates an example of a system for real-time visualization of brain activity. In the system of FIG. 4*a*, a detector comprises an inner ring detector 400 and an outer ring detector 300. The outer ring detector 300 is arranged circumferentially around the inner ring detector 400. The combined detector including Inner ring 400 and outer ring 300 may be made in accordance with the example shown in FIGS. 3*a*-3*f*.

A subject may be positioned with a portion of his/her body (e.g. his/her head) at least partially in the inner ring detector 400. The subject may have previously been administered a radioactive tracer comprising a radioisotope having a specific decay in which a positron and an additional gamma ray are emitted. The positron almost immediately annihilates with an electron to produce two back-to-back gamma rays. In total, there are thus three gamma rays, of which two move in opposite directions.

A researcher may expose a subject to different stimuli which may include visual, auditory and tactile stimuli or combinations thereof. In response to different stimuli, different parts or areas of the brain may be more active, attracting glucose. The radioactive tracers comprise glucose, and thus the radioactive tracers are concentrated in areas of increased brain activity. However, the same systems and methods may be useful for other PET imaging applications e.g. In oncology or pharmacokinetics.

Each of the systems 80 as illustrated in FIG. 3*c* may be connected to Digital Signal Processor 500. When using the built-up of the detector in accordance with the examples of FIGS. 3*a*-3*i*, no separate connections between the DSP and the inner detector are needed. All signals are transmitted at the second ends 13*b* of substrates 13.

The signals may comprise information as to in which voxel an impact was detected. The DSP 500 can from this Information calculate the origin of radioactive decay and send the information to display 600. Substantially in real time, 3D scatter plots of the intersection points between the LOR and Compton cone can be continuously reproduced.

Thanks to the additional information derived from the additional gamma ray, the origin of increased radioactive decay (and thus the area of increased brain activity) may be calculated more rapidly with the DSP and visualized substantially in real-time on display 600.

A researcher may thus adapt the stimuli to further investigate. In prior art systems, because of the delay involved in image reconstruction algorithms the valuable Information is not available as a researcher is investigating.

In some examples, a display for which the user can define the time window in which the data is accumulated and then displayed in real time. In order for the human eyes to see real time changes from one frame to another, the accumulation period may be around 20 msec, or 50 Hz.

Figure 4B:
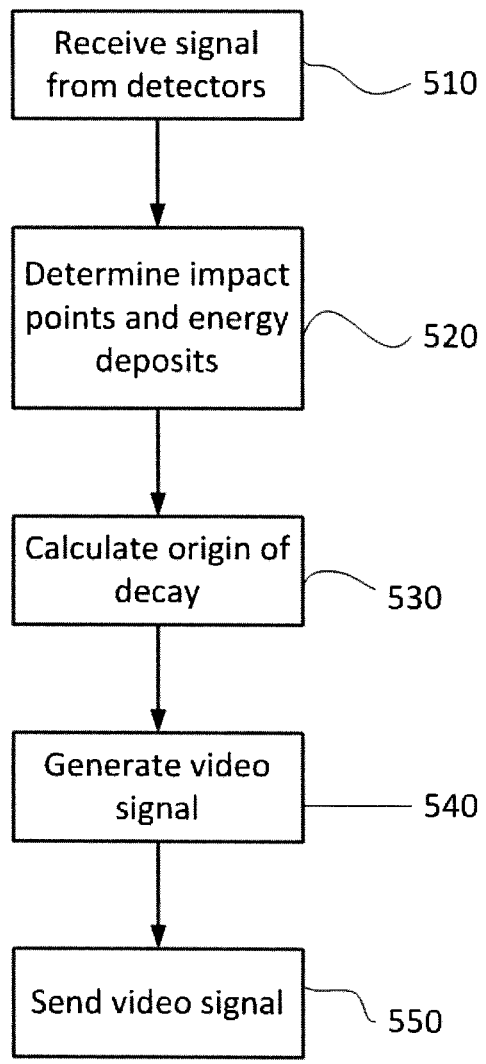

FIG. 4b schematically illustrates a process which may be used in a digital signal processor in examples of the system of FIG. 4a. At block 510, the signals may be received from the inner and outer detectors. These signals comprise information as to which voxel within each detector has detected an event and the corresponding time stamp. These signals may also comprise information as to the energy deposition of each of the impacts. At block 520, the geometric location of the points of impact may be calculated (this may be implemented e.g. as a look-up table linking each voxel to a specific geometric location) as well as the corresponding energy deposits.

At block 530, the origin of decay of specific events may be calculated. An example for doing this will be explained with reference to FIG. 4b. A video signal reflecting the origin of decay for these events can be generated at block 540. This video signal may then be sent at block 550 to a device capable of reproducing the video signal. e.g. a computer screen.

Figure 4C:
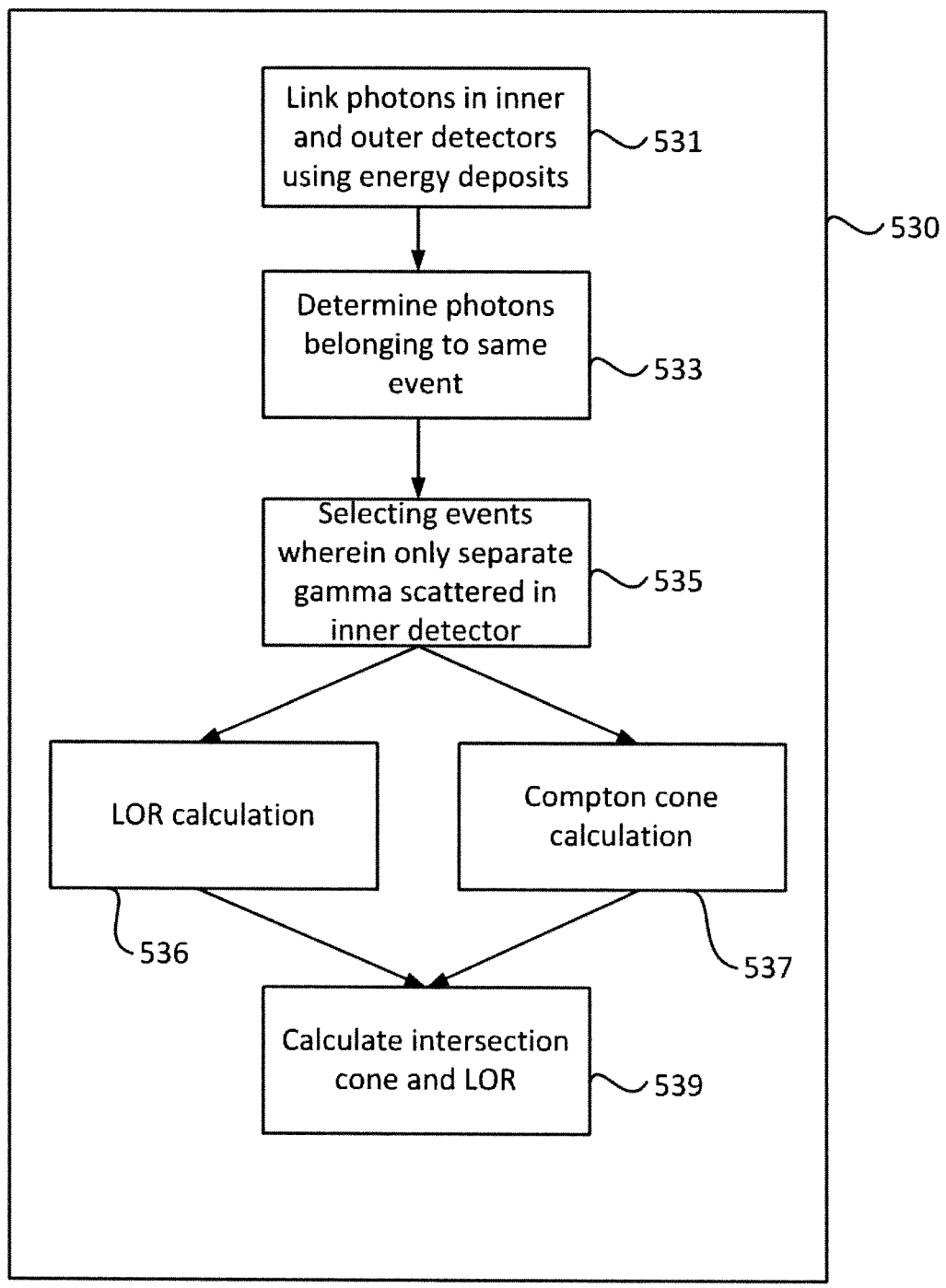
FIG. 4c schematically illustrates a process which may be used to calculate an origin of radioactive decay in examples of the present disclosure.

FIG. 4c schematically illustrates a process which may be used to calculate an origin of radioactive decay at block 530, also illustrated in FIG. 4b. At block 531, photons detected by the inner and outer detectors may be linked to each other by taking into account the energy deposits and the time coincidence. For example, back-to-back gamma rays each have an energy of 511 keV. A gamma ray that is scattered in the inner detector and is detected by both the inner and the outer detector will divide its energy between the inner and outer detector. The sum of the energy deposits thus has to be 511 keV if the gamma ray corresponds to one of the back-to-back gamma rays. On the other hand, if the gamma ray corresponds to the additional gamma ray as a direct result of the decay, its total energy will depend on the isotope used. For example, isotope $^{22}$Na has an additional high energy photon with an energy of 1274.5 keV, for isotope $^{44}$Sc this is 1157 keV and for $^{48}$V, this is 1312.1 keV. It will be clear that other isotopes might be used and that the corresponding energy for the chosen isotope will be known. Since the composition of the radioactive tracer is known, events that sum up to the correct amounts may be linked together. For example, in the case of $^{22}$Na, events for which the energy deposition in the inner detector and the outer detector sum up to 1274.5 keV can be linked together.

At block 533 photons that are detected within a short time span from each other, i.e. the same time window and satisfying the corresponding energy equation may be linked to each other and linked to the same event.

It is not necessary to calculate the origin of radioactive decay for every single event. In an example, only the events wherein the additional separate gamma ray is scattered in the inner detector and the back-to-back gamma rays are not scattered and only detected in the outer detector are selected. It is advantageous to select Inter alia these events because it is known that the photons detected in the inner and outer detector must satisfy the equations for Compton scattering, whereas the back-to-back gamma rays satisfy the equation governing the Line of Response. But The intersection of a Compton cone calculated at block 537 and the Line of Response calculated at 536 corresponds to the position of the origin of radioactive decay. This position may thus be calculated at block 539.

Details of the calculation of the intersection may be found in "*Using triple gamma coincidences with a pixelated semiconductor Compton-PET scanner: a simulation study*", M. Kolstein and M. Chmeissani, 17$^{th}$ International Workshop on Radiation Imaging Detectors.

In other examples, other events may (additionally) be selected. Events for which one or both of the two back-to-back gamma rays are detected in the inner ring and the outer ring may (also) be selected. The information from these events may also be used for the visualization of brain activity.

In yet further examples, yet other events may (additionally) be selected. Each type of event may satisfy different energy requirements and different geometric equations for the calculation of the origin of radioactive decay.

Figure 4D:
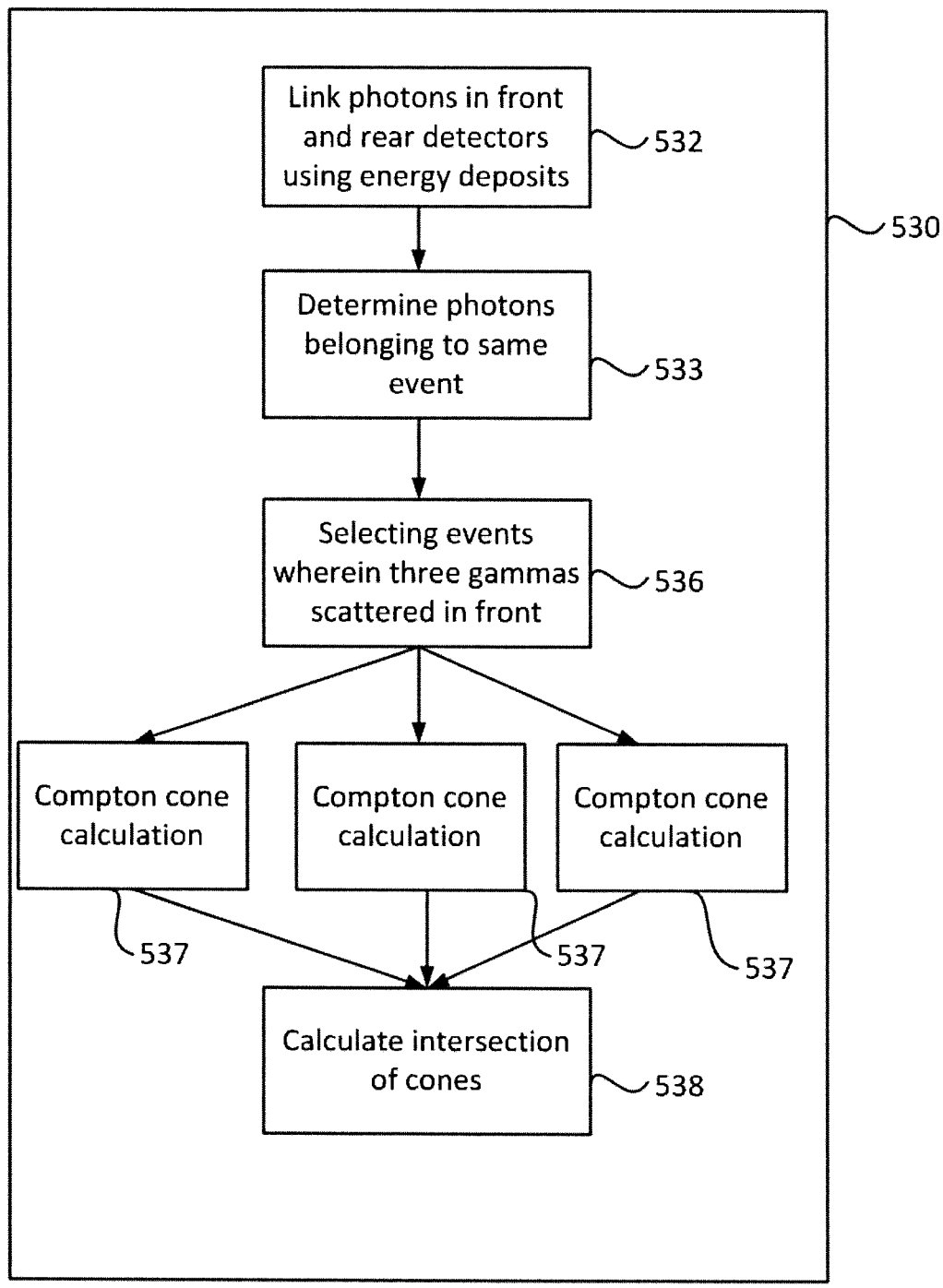
FIG. 4d schematically illustrates an alternative process which may be used to calculate an origin of radioactive decay in examples of the present disclosure.

FIG. 4d schematically Illustrates another example of visualization of radioactive decay in which a radioisotope with a different type of decay is shown. The detector used in this example may be a front detector and a rear detector, or an Inner and outer detector as in the previous example.

In the example of FIG. 4d, a subject may have been administered a radioisotope which in decay emits three separate gamma rays. The three gamma rays may have different energies. If the gamma rays scatter in the front detector and absorbed in the rear detector, events in the same time window can be linked together at block 523 by checking the energy deposits. Photons belonging to the same event can thus be determined at block 533.

At block 536, events wherein all three gamma rays are scattered in the front detector and absorbed in the rear detector can be selected. For each of the three gamma rays, Compton cone calculation for each of the three gamma rays can be performed at block 537. The three gamma rays that belong to a single event of decay can be combined to calculate the Intersection of the three Compron cones at block 538. The Intersection of the three cones gives the origin of a single event of decay. As the decay occurs, the event may be visualized.

Figure 5A:
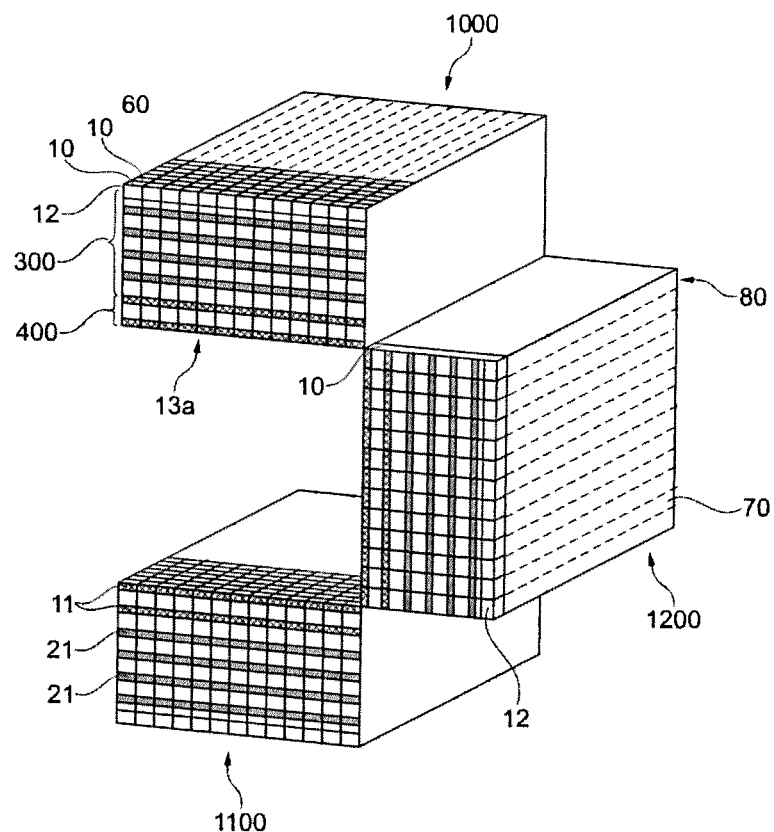
FIGS. 5a and 5b schematically illustrate a detector arrangement involving a plurality of detectors.
Figure 5B:
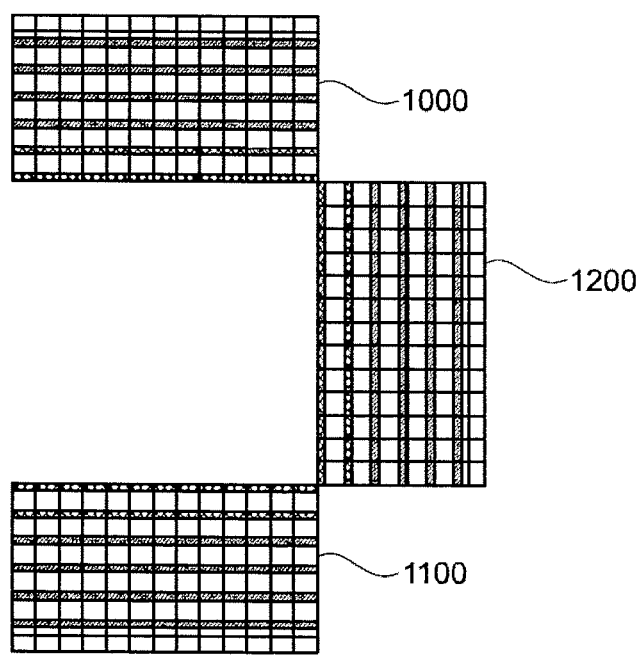

FIGS. 5a and 5b schematically illustrate an example of a detector arrangement. FIG. 5a provides an isometric view, whereas FIG. 5b provides a side view. In FIG. 5a, some continuous lines and some interrupted lines are used to indicate separate detector devices, detector modules, and detector systems which in reality are not necessarily visible in this way.

The detector arrangement of FIG. 5a includes a top detector 1000 a bottom detector 1100 and a side detector 1200. It is noted that even though a plurality of detectors Is used here in combination to provide more robust angle coverage, a single one of these detectors can function as a stand-alone Compton camera.

In the example arrangement of figure a, a subject or part of a subject of which imaging is to be performed is to be positioned in a space between the detectors 100, 1100 and 1200. The left side in the view of figure Sa is open for easier introduction of the body (part) of the subject for imaging. In an alternative example, a fourth detector may be arranged to provide a detector which Is substantially closed in cross-section.

Each of the detectors 1000, 1100 and 1200 include an inner detector 400 and an outer detector, the inner detector arranged closer to the subject. The inner detector 400 and outer detector 300 are formed by semiconductor slabs of detector devices which are similar to the detector devices illustrated with reference to FIG. 3a. In the example of figure Sa, the detector devices are substantially rectangular, rather than trapezoidal. Alternatively, also in this arrangement, trapezoidal detector devices could be used. When using trapezoidal detector devices, detector 1000 will take the shape of sector of hollow cylinder.

A group of semiconductor slabs 11 closer to the subject (i.e. closer to the first end 13a of the substrate) form the inner detector 400. These semiconductor slabs may be made from silicon. A group of semiconductor slabs 21 further away from the subject form the outer detector 300.

Each of the detectors 1000, 1100 and 1200 are constructed in a similar manner. A plurality of devices 10 comprising semiconductor slabs 11, 21 and input/output elements 12 are arranged on a substrate together form a module 60 having a single Interface. A number of modules 60 may be grouped together to from a system 80 sharing an interface bus, which may be a printed circuit board (PCB).

FIGS. 6a-6c schematically illustrate a further example of a detector device 10' which may be used to build up detectors and may be used in methods disclosed herein. FIG. 6a provides an isometric view, FIG. 6b a side view and FIG. 6c a top view.

In contrast to the detector devices illustrated in FIG. 3, the detector device 10b of this example has a substrate 13 and semiconductor slabs are provided on top side 18 and on bottom side 19. A single detector device 10b is formed in this case by providing two rows of solid-state detectors 11, 21 on a single device. The semiconductor detectors are mounted on a base layer 13. For each row of semiconductor detectors, an input/output element 12 is provided. An advantage of this design of the device is that slab 11 can be made thinner for better charge collection, than when two devices 10 according to FIG. 3a are combined.

The semiconductor slabs 11 closer to first end 13a together form the inner detector 400, and semiconductor slabs 21 closer to the second end together from the outer selector 300. FIG. 6c schematically illustrates interface 61 which may be shared by a plurality of devices 10b.

For completeness, various aspects of the present disclosure are set out in the following numbered clauses:

Clause 1. Method for real-time visualization of metabolic activity in a subject, wherein the subject has previously been administered a radioactive tracer and positioned such that a portion of a body of the subject is at least partially provided within a photon detector, the method comprising
 detecting radioactive decay of the tracer within the photon detector FOV;
 calculating a position of an origin of the radioactive decay; and
 displaying the position of the origin of the radioactive decay substantially in real-time, wherein
 the radioactive tracer comprises a radioactive isotope which in decay emits a positron and a separate gamma ray, and
 the photon detector comprises an inner ring detector, and an outer ring detector,
 the detecting with the photon detector comprises detecting photons originating from two back-to-back gamma rays resulting from positron-electron annihilation and the separate gamma ray in the inner and the outer ring detector, and
 the calculating the position of the origin of the radioactive decay comprises
  determining impacts of photons in the inner and outer ring detectors belonging to the same event of radioactive decay, wherein the separate gamma ray is detected in both the inner and the outer ring detector and
  in relation with the impacts belonging to the same event of radioactive decay using Line-of-Response calculation and Compton cone calculation based on Compton scattering from the inner ring detector.

Clause 2. Method according to clause 1, wherein the radioactive isotope is one or more of the following: $^{22}$Na, $^{44}$Sc, $^{48}$V.

Clause 3. Method according to clause 1 or 2, wherein the calculating the position of the origin of the radioactive decay furthermore comprises determining energy deposits of the impacts belonging to the same event.

Clause 4. Method according to clause 3, wherein the using Compton cone calculation comprises
 determining an energy deposit of a first photon in the inner ring detector and an energy deposit of a second photon in the outer ring detector and
 linking the first and second photons to a single gamma ray.

Clause 5. Method according to clause 4, further comprising selecting events in which the two back-to-back gamma rays are detected in the outer ring, and the separate gamma ray scatters in the inner detector and Is detected both in the inner and in the outer detector.

Clause 6. Method according to clause 4 or 5, further comprising selecting events in which at least one of the two back-to-back gamma rays Is detected in both the inner and the outer ring detector and a sum of the energy deposits in the inner and outer ring detector is 511 keV.

Clause 7. Method according to any of clauses 1-6, wherein the inner and the outer ring detectors are semiconductor detectors, in particular pixelated semiconductor detectors.

Clause 8. Method according to clause 7, wherein the inner and the outer ring detectors are voxelated semiconductor detectors.

Clause 9. Method for real-time monitoring of activity in a brain of a subject which has previously been administered a radioactive tracer, the method comprising:
 positioning the subject such that the brain of the subject is at least partially provided within a photon detector;
 providing a stimulus to the subject and
 a method for real-time visualization according to any of clauses 1-8.

Clause 10. Method according to clause 9, wherein the stimulus comprises one or more of a tactile, visual and auditory stimulus.

Clause 11. System for real-time visualization of metabolic activity in a subject which has previously been administered a radioactive tracer comprising
 a photon detector comprising an Inner ring detector, and an outer ring detector,
 a computing system for determining at least four impacts of photons in the inner and outer ring detectors, for calculating a position of an origin of the radioactive decay using in relation with the at least four impacts Line-of-Response calculation and Compton cone calculation based on Compton scattering from the first detector, and for generating a video signal reflecting the origin of the radioactive decay, and
 a device capable of receiving the video signal and reproducing the video signal on a screen.

Clause 12. System according to clause 11, wherein the inner ring detector and the outer ring detector are pixelated semiconductor detectors.

Clause 13. System according to clause 11 or clause 12, wherein the computing system is a digital signal processor connected with the inner and the outer ring detectors.

Clause 14. System according to any of clauses 11-13, further comprising a head support for securely positioning a head of the subject with respect to the photon detector.

Clause 15. System according to any of clauses 11-14, wherein a distance between an inner rim of the outer ring detector and an outer rim of the inner ring detector is at least 5 cm, and preferably 10 cm or more.

Clause 16. A detector comprising
an inner ring detector, and an outer ring detector,
the inner ring detector and the outer ring detector being formed by a plurality of detector modules arranged to form substantially a ring shape,
wherein the detector modules comprise one or more detector devices, the detector devices having a substrate upon which a plurality of semiconductor detector slabs are arranged,
wherein the inner ring detector comprises one or more of the semiconductor detector slabs, and the outer ring detector comprises one or more others of the semiconductor detector slabs.

Clause 17. Detector according to clause 16, wherein the substrate is a kapton layer.

Clause 18. Detector according to clause 16 or clause 17, wherein the detector devices comprise a readout circuit for each of the detector slabs, the readout circuits being arranged on the substrate, and the detector slabs being arranged on the readout circuits.

Clause 19. Detector according to clause 18, wherein the readout circuits are ASICs.

Clause 20. Detector according to any of clauses 16-19, wherein the detector slabs of the inner detector are made from silicon, and the detector slabs of the outer detector are made from CdTe.

Clause 21. Detector according to any of clauses 16-19, wherein the detector slabs of the inner detector and the detector slabs of the outer detector are made of the same material.

Clause 22. A detector for detecting photons comprising
a plurality of detector modules forming a front detector and a rear outer detector,
the detector modules comprising a plurality of detector devices, and an interface.
the detector devices having a substrate extending from a front end to a rear end, and carrying a plurality of pixelated semiconductor detector slabs, and being arranged such that the front end is closer to a source of the photons than the rear end,
the semiconductor detector slabs being arranged on readout circuits, and the detector devices having an input/output element at or near the rear end of the substrate,
wherein a front group of one or more of the semiconductor detector slabs arranged close to the front end of the substrate are made from a semiconductor material configured to promote photon scattering and form the front detector,
wherein a rear group of one or more of the semiconductor detector slabs arranged closer to the rear end of the substrate than the front group are made from a semiconductor material configured to promote photon absorption, and form the rear detector.

Clause 23. Detector according to clause 22, wherein the substrate is a kapton layer, and wherein optionally the read-out circuits are ASICs.

Clause 24. Detector according to clause 21 or 22, wherein a distance between the rearward most detector slab of the front detector and the forward most detector slab of the rear detector is greater than a distance between the detector slabs of the front detector and than a distance between the detector slabs of the rear detector.

Clause 25. Detector according to clause 24, wherein the distance between the rearward most detector slab of the front detector and the forward most detector slab of the rear detector is between 5 and 30 centimetres, specifically between 10 and 20 centimetres.

Clause 26. Detector according to any of clauses 22-25, wherein a distance between the detector slabs of the front detector is between 0.5 and 2 centimetres.

Clause 27. Detector according to any of clauses 22-27, wherein a distance between the detector slabs of the rear detector is between 0.5 and 2 centimetres.

Clause 28. Detector according to any of clauses 22-27, wherein the detector slabs of the front detector are made from silicon.

Clause 29. Detector according to any of clauses 22-28, wherein the detector slabs of the rear detector are made from CdTe, CdZnTe, $HgI_2$, TiBr, GaAs, PbS or $CaTiO_3$.

Clause 30. Detector according to any of clauses 22-29, which is a PET detector, wherein the front detector and rear detector have a substantially circular cross-section, and wherein the substrates have a isosceles trapezoidal shape.

Clause 31. Detector according to any of clauses 22-29, wherein the substrates have a substantially rectangular shape.

Clause 32. A Compton camera comprising a detector according to clause 31.

Clause 33. System for real-time visualization of metabolic activity in a subject which has previously been administered a radioactive tracer comprising
a detector according to any of clauses 22-32,
a computing system for determining impacts of photons in the front and rear detectors, for calculating a position of an origin of the radioactive decay using in relation with the impacts Line-of-Response calculation and/or Compton cone calculation based on Compton scattering from the front detector, and for generating a video signal reflecting the origin of the radioactive decay, and
a device capable of receiving the video signal and reproducing the video signal on a screen.

Clause 34. System according to clause 33, wherein the computing system is a digital signal processor connected with the Interfaces of the detector modules.

Clause 35. A detector for detecting photons comprising
a plurality of detector modules forming a front detector and a rear detector,
the detector modules comprising a plurality of detector devices, and an interface,
the detector devices having a substrate extending from a front end to a rear end, and carrying a plurality of pixelated semiconductor detector slabs, and being arranged such that the front end is closer to a source of the photons than the rear end,
the semiconductor detector slabs being arranged on readout circuits, and the detector devices having an input/output element at or near the rear end of the substrate,
wherein a front group of one or more of the semiconductor detector slabs arranged close to the front end of the substrate form the front detector, wherein a rear group of one or more of the semiconductor detector slabs arranged closer to the rear end of the substrate than the front group form the rear detector, and wherein a distance between the rearward most detector slab of the inner detector and the forward most detector slab of the rear detector is greater than a distance between the detector slabs of the front detector and than a distance between the detector slabs of the rear detector.

Clause 36. Detector according to clause 35, wherein the distance between the rearward most detector slab of the front detector and the forward most detector slab of the rear detector is between 5 and 30 centimetres, specifically between 10 and 20 centimetres.

Clause 37. Detector according to clause 35 or 36, wherein a front group of one or more of the semiconductor detector slabs arranged close to the front end of the substrate are made from a semiconductor material configured to promote photon scattering, and wherein a rear group of one or more of the semiconductor detector slabs arranged closer to the rear end of the substrate than the front group are made from a semiconductor material configured to promote photon absorption.

Clause 38. Detector according to any of clauses 35-37, wherein a distance between the detector slabs of the front detector is between 0.5 and 2 centimetres.

Clause 39. Detector according to any of clauses 35-38, wherein a distance between the detector slabs of the rear detector is between 0.5 and 2 centimetres.

Clause 40. Detector according to any of clauses 35-39, wherein the detector slabs of the front detector are made from silicon.

Clause 41. Detector according to any of clauses 35-40, wherein the detector slabs of the rear detector are made from any of GaAs, CdTe, CdZnTe, TlBr, PbS, CaTiO3 or HgI2.

Clause 42. Detector according to any of clauses 35-41, wherein the readout circuits are ASICs.

Clause 43. Detector according to any of clauses 35-42, wherein the front detector and rear detector have a substantially circular cross-section, and wherein the substrates have an isosceles trapezoidal shape.

Clause 44. Detector according to any of clauses 35-42, wherein the substrates have a substantially rectangular shape.

Although only a number of examples have been disclosed herein, other alternatives, modifications, uses and/or equivalents thereof are possible. Furthermore, all possible combinations of the described examples are also covered. Thus, the scope of the present disclosure should not be limited by particular examples, but should be determined only by a fair reading of the claims that follow.

The invention claimed is:

1. A detector for detecting photons comprising
a plurality of detector modules forming a front detector and a rear detector,
the detector modules comprising a plurality of detector devices, and an interface,
the detector devices having a substrate extending from a front end to a rear end, and carrying a plurality of pixelated semiconductor detector slabs, and being arranged such that the front end is closer to a source of the photons than the rear end,
the semiconductor detector slabs being arranged on readout circuits, and the detector devices having an input/output element at or near the rear end of the substrate,
wherein a front group of one or more of the semiconductor detector slabs arranged close to the front end of the substrate are made from a low Z semiconductor material configured to promote photon scattering and form the front detector,
wherein a rear group of one or more of the semiconductor detector slabs arranged closer to the rear end of the substrate than the front group are made from a high Z semiconductor material configured to promote photon absorption, and form the rear detector.

2. The detector according to claim 1, wherein the substrate is a kapton layer.

3. The detector according to claim 1, wherein a distance between the rearward most detector slab of the inner detector and the forward most detector slab of the rear detector is greater than a distance between the detector slabs of the front detector and than a distance between the detector slabs of the rear detector.

4. The detector according to claim 3, wherein the distance between the rearward most detector slab of the front detector and the forward most detector slab of the rear detector is between 5 and 30 centimetres, specifically between 10 and 20 centimetres.

5. The detector according to claim 1, wherein the front detector comprises a plurality of detector slabs and a distance between the detector slabs of the front detector is between 0.5 and 2 centimeters.

6. The detector according to claim 1, wherein the rear detector comprises a plurality of detector slabs and a distance between the detector slabs of the rear detector is between 0.5 and 2 centimeters.

7. The detector according to claim 1, wherein the detector slabs of the front detector are made from silicon.

8. The detector according to claim 7, wherein the detector slabs of the rear detector are made from CdTe, CdZnTe, GaAs, T1Br, PbS, CaTiO3 or HgI2.

9. The detector according to claim 1, wherein the readout circuits are ASICs.

10. The detector according to claim 1, wherein the front detector and rear detector have a substantially circular cross-section, and wherein the substrates have an isosceles trapezoidal shape.

11. The detector according to claim 1, wherein the substrates have a substantially rectangular shape.

12. A Compton camera comprising the detector according to claim 11.

13. A system for real-time visualization of metabolic activity in a subject which has previously been administered a radioactive tracer comprising
the detector according to claim 10,
a computing system for determining impacts of photons in the front and rear detectors, for calculating a position of an origin of the radioactive decay using in relation with the impacts Line-of-Response calculation and/or Compton cone calculation based on Compton scattering from the front detector, and for generating a video signal reflecting the origin of the radioactive decay, and
a device capable of receiving the video signal and reproducing the video signal on a screen.

14. The system according to claim 13, wherein the computing system is a digital signal processor connected with the interfaces of the detector modules.

15. A method for real-time visualization of metabolic activity in a subject, wherein the subject has previously been administered a radioactive tracer and positioned such that a portion of a body of the subject is at least partially provided within a photon detector according to claim 1, the method comprising detecting radioactive decay of the tracer within the photon detector FOV;

calculating a position of an origin of the radioactive decay; and displaying the position of the origin of the radioactive decay substantially in real-time, wherein the radioactive tracer comprises a radioactive isotope which in decay emits a positron and a separate gamma ray, the detecting with the photon detector comprises detecting photons originating from two back-to-back gamma rays resulting from positron-electron annihilation and the separate gamma ray in the inner and the outer ring detector, and the calculating the position of the origin of the radioactive decay comprises determining impacts of photons in the front and rear detectors belonging to the same event of radioactive decay, wherein the separate gamma ray is detected in both the front and rear detectors and in relation with the impacts belonging to the same event of radioactive decay using Line-of-Response calculation and Compton cone calculation based on Compton scattering from the front detector.

16. The method according to claim 15, wherein the radioactive isotope is one or more of the following: $^{22}$Na, $^{44}$Sc, $^{48}$V.

17. The method according to claim 15, wherein the calculating the position of the origin of the radioactive decay furthermore comprises determining energy deposits of the impacts belonging to the same event.

18. The method according to claim 15, wherein the using Compton cone calculation comprises determining an energy deposit of a first photon in the front detector and an energy deposit of a second photon in the rear detector and linking the first and second photons to a single gamma ray.

19. A method for real-time monitoring of activity in a brain of a subject which has previously been administered a radioactive tracer, the method comprising:

positioning the subject such that the brain of the subject is at least partially provided within the photon detector;

providing a stimulus to the subject; and the method for real-time visualization according to claim 15.

20. The method according to claim 19, wherein the stimulus comprises one or more of a tactile, visual and auditory stimulus.

\* \* \* \* \*